Dec. 3, 1957 J. D. BATTAGLIA Plant Pat. 1,661
PEACH TREE
Filed Feb. 14, 1957 2 Sheets-Sheet 1
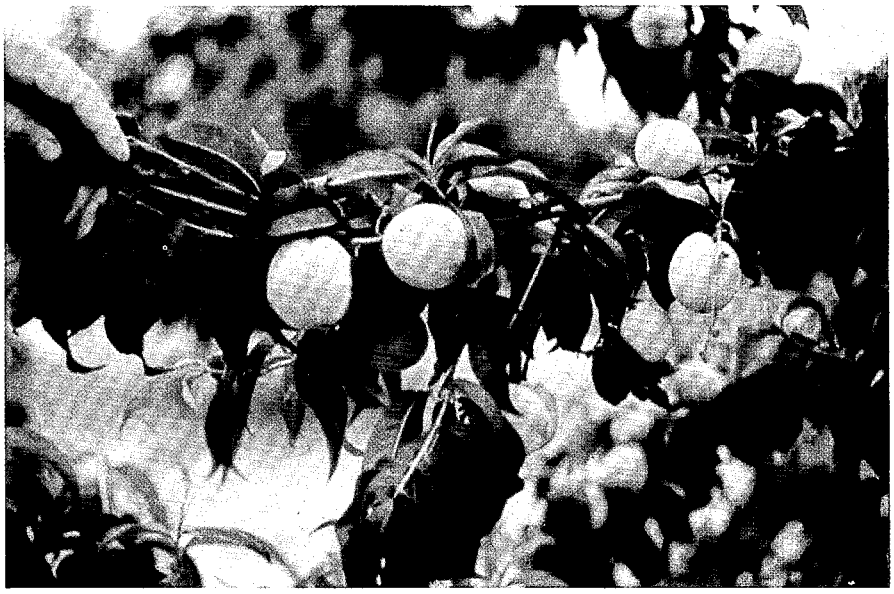
INVENTOR
Joseph D. Battaglia
BY Robert Cobb
ATTORNEYS PEACH TREE
Filed Feb. 14, 1957 2 Sheets-Sheet 2
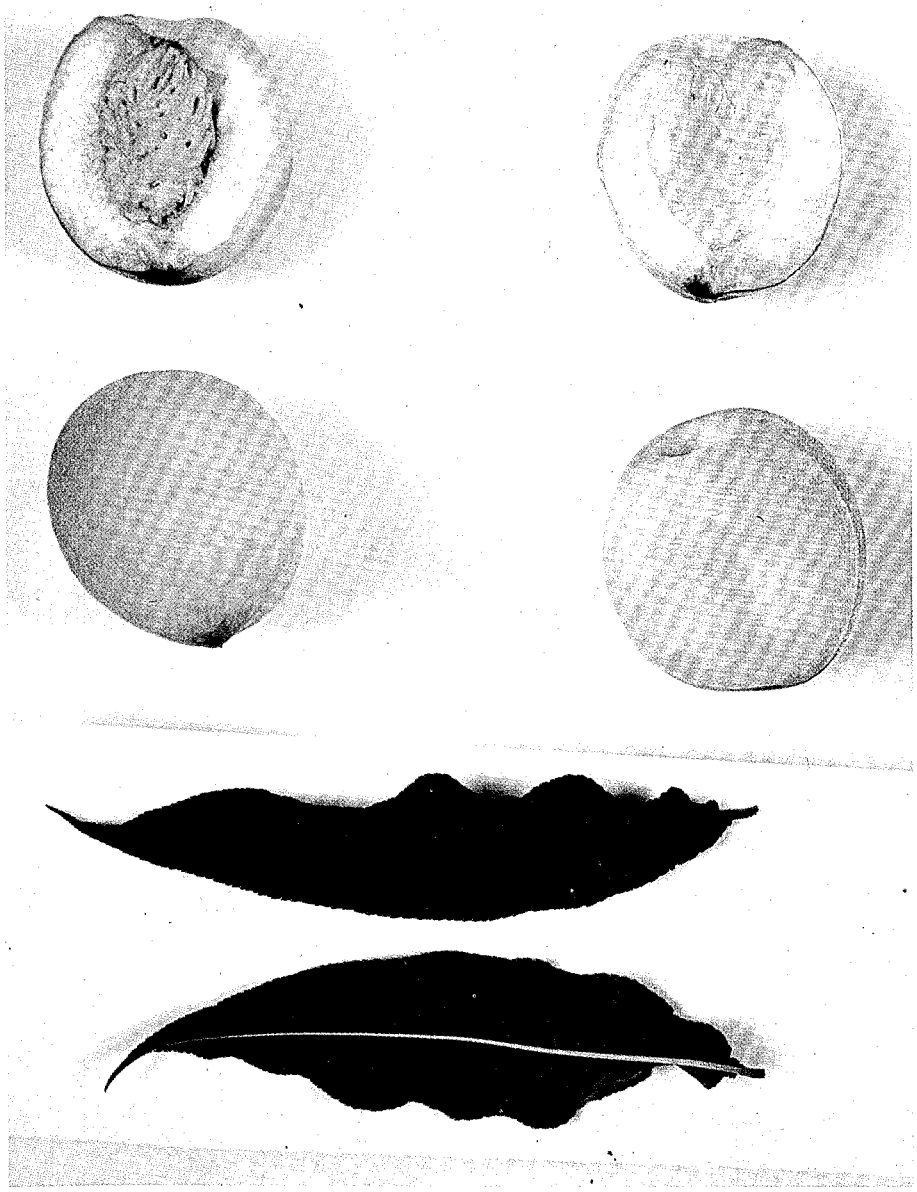
INVENTOR
Joseph D. Battaglia
BY Robert Cobb
ATTORNEYS United States Patent Office Plant Pat. 1,661
Patented Dec. 3, 1957

1,661

PEACH TREE

Joseph D. Battaglia, Hammonton, N. J., assignor to Edgar H. Kemp and Homer S. Kemp, Princess Anne, Md., copartners, trading as Bountiful Ridge Nurseries Application February 14, 1957, Serial No. 640,299

1 Claim. (Cl. 47—62)

The present invention relates to a new and distinct variety of peach tree which was discovered by me as a sport of the variety known as "Erly-Red-Fre" (Plant Patent No. 320), in my cultivated orchard near Hammonton, Atlantic County, New Jersey.

At the time of my discovery, my attention was attracted to a particular tree of "Erly-Red-Fre" which appeared to be ripening unusually early and bearing fruit that was somewhat different from the normal fruit of this parent variety. On closer observation, I found that the tree had sported, and I thereupon took steps to preserve the sport, keep it under close observation, and to asexually reproduce the same, as performed by budding.

Continued tests and observations of the new sport have conclusively shown and demonstrated that it is new and distinct from its parent, as well as differentiated from all other varieties of which I am aware, as evidenced by the following characteristics which are outstanding in the new sport:

(1) Vigorous and sturdy habits of growth;

(2) Prolific fruit-bearing habit when young;

(3) Early ripening of the fruit—approximately three weeks earlier than the fruit of the parent variety "Erly-Red-Fre," and about the same as or slightly earlier than the variety "Mayflower" (unpatented);

(4) Large size of the fruit;

(5) Early, uniform, high coloring of the fruit which may be generally described as Bright Red with a Creamy White background;

(6) Semi-freestone habit of the fruit;

(7) Good flavor of the fruit; and (8) Good shipping qualities of the fruit.

Asexual reproduction of the new sport by budding, as performed at Hammonton, New Jersey, shows that the foregoing characteristics and distinctions come true to form and are established and transmissible through succeeding propagations.

The accompanying drawings show typical specimens of the foliage and fruit of my new variety in different stages of development and as depicted in color as nearly true as it is reasonably possible to make the same in color illustrations of this character, one of said drawings showing foliage and fruit specimens on an enlarged scale, with one of the fruit specimens depicted in cross-section.

The following is a detailed description of the new variety, with color terminology in accordance with general color terms of ordinary significance and/or Maerz and Paul Dictionary of Color:

(Observations made from specimens grown near Hammonton, New Jersey.)

Dates first and last picking: About June 21st and June 30th, respectively.

Tree: Large; vigorous; spreading; open; vase-formed; hardy; very productive; regular bearer.

Trunk.—Stocky; medium smoothness.

*Branches.*—Medium caliper; medium smoothness. Color—Glossy Brown, Plate 8, Color C–5 in the case of 1-year old wood, and Madura, Plate 14, Color I–8 in the case of 2-year old wood. Lenticels—Medium number; medium size.

*Leaves.*—Large; length from about 5 to 6 inches; width from about 1½ to 1¾ inches; oval; lanceolate; acutely pointed; medium thickness; smooth. Color—upper side: Polo Green, Plate 23, Color J–9; under side: Hellebore Green, Plate 23, Color L–3. Margin—Crenate; doubly serrate. Petiole—Medium length; medium thickness. Glands—Average number two; opposite; medium size; globose; positioned at base of blade. Color—Green. Stipules—None.

Buds: Hardy; medium size; medium length; conic; plump; from appressed to free; pubescent.

Flowers: Dates of first and full bloom—About April 7th and April 11th, respectively; considered as medium to late.

*Size.*—Medium.

*Color.*—Salmon, Plate 43, Color J–1.

Fruit: Maturity when described—eating over-ripe. Date—July 8th.

*Size.*—Uniform; large. Axial diameter—about 2¼ inches. Transverse diameter in suture plane—about 2⅜ inches. Diameter at right angles to suture plane—about 2¼ inches.

*Form.*—Uniform; symmetrical; oblong; broadly ovoid; compressed laterally toward suture.

*Suture.*—Distinct; shallow; extends from base, but discontinues at apex; has slight marked depression beyond pistil point.

*Ventral surface.*—Rounded slightly; lipped toward base; lips equal.

*Cavity.*—Flaring; abrupt; elongated in suture plane, with suture showing on one side. Depth—from about ¼ to ⅜ inch. Breadth—about ½ inch. Markings—none.

*Base.*—Rounded.

*Apex.*—Short; mammiform; rounded; oblique pistil point.

*Stem.*—About ½ inch long; medium caliper; glabrous; medium adherence to stone.

*Skin.*—Medium thickness; tough; tenacious to flesh; no tendency to crack in wet seasons. Color—Cream, Plate 9, Color G–3, with Troubador Red blush, Plate 3, Color L–8. Down—from moderate to scant; medium length; does not roll up when rubbed.

*Flesh.*—Color—Creamy White, mottled with Red next to skin on sunny side.

*Surface of pit cavity.*—Color—Pale White, with White fibers.

*Amydgalin.*—Wanting.

*Juice.*—Abundant; from rich to watery.

*Texture.*—Firm; fine; meaty; melting.

*Fibers.*—Few; fine; tender.

*Ripens.*—Evenly.

*Flavor.*—Subacid; mild; vinous.

*Aroma.*—Distinct.

*Eating quality.*—Good.

Stone: Semi-free; adheres to flesh slightly over entire surface.

*Fibers.*—Short; free; retains short fiber-like threads along ridges.

*Size.*—Small. Length—from about 1⅛ to 1¼ inches. Breadth—from about ¾ to 1 inch. Thickness—from about ½ to ⅝ inch.

*Form.*—Oval.

*Base.*—Oblique.

*Hilum.*—Narrow; oblong.

*Apex.*—Acuminate.

*Sides.*—Unequal; curved on right side.
*Surface.*—Regularly furrowed near base; ridged near base.
*Ridges.*—Rounded.
*Pits.*—Elongated.
*Ventral edge.*—Thin; with wing toward base.
*Dorsal edge.*—Full; with shallow, narrow groove toward base.
*Ridges on either side.*—Continuous.

Disease Resistance: Good resistance to bacterium pruni as determined by comparison with other varieties which were quite susceptible to this disease when grown under comparable cultural conditions at Hammonton, New Jersey.

Use: Market; local; dessert.
Keeping quality: Good.
Shipping quality: Good.

I claim:

A new and distinct variety of peach tree of the semi-freestone type, substantially as herein shown and described, characterized particularly as to novelty by its vigorous and sturdy growth, its prolific fruit-bearing habit when young, the early ripening habit of its fruit, the large size of its fruit, the early, uniform high coloring of its fruit, and the good flavor and good shipping qualities of its fruit.

No references cited.